US011071864B2

(12) United States Patent
Boor et al.

(10) Patent No.: US 11,071,864 B2
(45) Date of Patent: Jul. 27, 2021

(54) APPARATUS AND METHOD FOR PROVIDING SPLIT STIMULATION CURRENTS IN A PULSE GENERATOR

(71) Applicant: ADVANCED NEUROMODULATION SYSTEMS, INC., Plano, TX (US)

(72) Inventors: Steven Boor, Plano, TX (US); Daran DeShazo, Lewisville, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 94 days.

(21) Appl. No.: 16/189,746

(22) Filed: Nov. 13, 2018

(65) Prior Publication Data

US 2020/0147389 A1    May 14, 2020

(51) Int. Cl.
*A61N 1/36* (2006.01)
*A61N 1/378* (2006.01)
*A61N 1/372* (2006.01)

(52) U.S. Cl.
CPC ..... *A61N 1/36125* (2013.01); *A61N 1/36062* (2017.08); *A61N 1/378* (2013.01); *A61N 1/3615* (2013.01); *A61N 1/36071* (2013.01); *A61N 1/37211* (2013.01)

(58) Field of Classification Search
CPC .................................................. A61N 1/36062
See application file for complete search history.

(56) References Cited

U.S. PATENT DOCUMENTS

| | | | |
|---|---|---|---|
| 6,609,031 B1 | 8/2003 | Law et al. | |
| 6,609,032 B1* | 8/2003 | Woods | A61N 1/36071 |
| | | | 607/46 |
| 7,180,760 B2 | 2/2007 | Varrichio et al. | |
| 7,212,110 B1 | 5/2007 | Martin et al. | |
| 7,228,179 B2 | 6/2007 | Campen et al. | |
| 7,571,007 B2 | 8/2009 | Erickson et al. | |
| 7,751,879 B2 | 7/2010 | Varrichio et al. | |
| 7,949,393 B2 | 5/2011 | Varrichio et al. | |
| 9,844,661 B2 | 12/2017 | Franz et al. | |
| 2005/0245977 A1 | 11/2005 | Varrichio et al. | |
| 2006/0170486 A1 | 8/2006 | Tranchina et al. | |
| 2009/0048643 A1 | 2/2009 | Erickson et al. | |
| 2009/0326608 A1 | 12/2009 | Huynh et al. | |
| 2010/0125315 A1* | 5/2010 | Parramon | A61N 1/36157 |
| | | | 607/59 |

(Continued)

FOREIGN PATENT DOCUMENTS

WO     01/93953 A1    12/2001

*Primary Examiner* — Rex R Holmes
*Assistant Examiner* — Jennifer L Ghand

(57) ABSTRACT

An apparatus and method for providing split stimulation currents in a pulse generator. In one embodiment, a current regulator of the pulse generator includes a digitally-programmable analog voltage generator coupled to a first input of an error amplifier that receives a second input controlled by a programmable resistor network configured to control a programmable total stimulation current output. A plurality of current splitting switches are operative to split the programmable total stimulation current output into a corresponding plurality of split current segments, which may be individually mapped to a selected set of lead electrodes across one or more implantable leads associated with the pulse generator.

25 Claims, 9 Drawing Sheets

(56) References Cited

U.S. PATENT DOCUMENTS

| | | | |
|---|---|---|---|
| 2011/0066407 A1* | 3/2011 | Butson | A61B 5/7257 |
| | | | 703/2 |
| 2011/0072657 A1 | 3/2011 | Swanson et al. | |
| 2014/0343564 A1 | 11/2014 | Feler et al. | |
| 2014/0343628 A1* | 11/2014 | Kaula | G06F 3/0484 |
| | | | 607/59 |
| 2016/0008601 A1* | 1/2016 | Meadows | A61N 1/0556 |
| | | | 607/59 |
| 2016/0339245 A1* | 11/2016 | Mauger | A61N 1/36038 |
| 2018/0008821 A1 | 1/2018 | Gonzalez et al. | |
| 2019/0329039 A1* | 10/2019 | Marnfeldt | A61N 1/36196 |

* cited by examiner

APPARATUS AND METHOD FOR PROVIDING SPLIT STIMULATION CURRENTS IN A PULSE GENERATOR

TECHNICAL FIELD

The present disclosure generally relates to implantable pulse generators and circuitry used in association with neurostimulation systems (NS) including but not limited to spinal cord stimulation (SCS) systems.

BACKGROUND

The use of electronic stimulation systems to control pain or other indications, or to otherwise provide therapy, by nerve or muscle stimulation has been in use for a number of years. For example, spinal cord stimulation (SCS) is a technique that has been used for pain management since the 1960s, Stimulation systems may also be used in stimulating areas other than the spinal cord, such as for deep brain stimulation, muscle stimulation, etc.

Stimulation systems often comprise a pulse generator coupled to one or more therapy delivery leads having a plurality of electrodes disposed in an area in which neurostimulation is desired. Alternatively, stimulation systems may comprise a micro-stimulation system in which a small implantable housing having electrodes thereon includes a pulse generator, wherein the entire micro-stimulation system is disposed in an area in which neurostimulation is desired. Of course, all or a portion of a stimulation system need not be implanted into a body to provide a desired therapy.

A stimulation system pulse generator may be provided in various configurations, such as a totally implanted pulse generator (IPG) or a radio frequency (RF)-based system. A typical IPG configuration comprises a surgically implanted, internally-powered pulse generator and one or more multi-electrode leads. A typical RF system configuration comprises a surgically implanted, passive receiver and a transmitter which is worn externally. In operation, the transmitter communicates, through an RF signal, to the implanted receiver to provide stimulation energy and control.

In an SCS application, electrodes used with an example pulse generator, such as any of the foregoing pulse generators, deliver a particularized electric field to a specific region of the spinal cord or surrounding tissue. Applying such an electric field across one or more nerve bundles and/or nerve roots, if properly directed and produced at the necessary levels, can "mask" certain forms of chronic pain in a phenomenon referred to as "paresthesia". Similarly, applying an electric field across other tissue, such as muscle or brain matter, near which such electrodes are disposed may provide a desired therapy. The focus, characteristics and intensity of the generated electric field are determined by the electrode configuration (the polarity, if any, assumed by each electrode) and the properties of an electric pulse waveform, which may generally include a stimulation frequency, a stimulation pulse width, a stimulation pulse amplitude, discharge method, and phase information, etc. (collectively "stimulation settings" or "stimsets").

Implantation of all or a portion of a stimulation system, e.g., a stimulation system including a fully implanted IPG or a RF system receiver/transmitter, necessarily requires a neurostimulation patient to undergo an implantation surgery. Additionally, routing a lead subdermally between an implanted pulse generator and the tissue area to be stimulated typically requires a relatively invasive procedure, such as a tunneling procedure. Likewise, explanting all or a portion of a stimulation system requires a neurostimulation patient to again undergo the trauma of surgery.

Due to possible misalignment/misplacement and/or shifting of implantable lead electrodes relative to the target region in a patient, it is desirable to make fine-tuned adjustments in the shape of the electric field in the patient for optimizing the delivered stimulation current therapy from an implantable stimulation system.

Whereas advances in IPG systems for use with NS systems continue to grow apace, several lacunae remain, thereby requiring further innovation as will be set forth hereinbelow.

SUMMARY

Embodiments of the present patent disclosure are broadly directed to IPG systems and associated circuitry wherein adjustments of an applied electric field proximate to the stimulation target area of a patient can be advantageously effectuated for a misaligned or shifted lead by providing simultaneous splitting of the stimulation current to multiple electrodes, which may be spatially separated in near-proximity to the stimulation target area.

In one aspect, an embodiment of the present disclosure is directed to a pulse generator for stimulating biological tissue, comprising, inter alia, a power supply module and a processing unit operative with a digital control logic module to provide control signals to a current regulator configured to split a stimulation current into a plurality of split current segments. In one arrangement, the current regulator comprises a digitally-programmable analog voltage generator operative with the power supply module to provide a voltage output signal to a first input of an error amplifier configured to generate a programmable total stimulation current output. A programmable resistor network is configured to control an input signal provided to a second input of the error amplifier responsive to the programmable total stimulation current output. A plurality of current splitting switches are operative to split the programmable total stimulation current output into a corresponding plurality of split current segments, which may be individually mapped or routed by a current mapping/routing control module configured to selectively connect each split current segment to one or more electrodes of an implantable lead system comprising one or more leads, each having a plurality of electrodes. Accordingly, an electrode of a select lead may be selectively activated to apply a fraction of the total stimulation current output for stimulating the biological tissue depending on an electrical connection relationship determined by the current mapping control module. In one variation, depending on whether the electrodes are programmed as cathodes or anodes, an embodiment of a current regulator may be configured to split either cathodic stimulation current or anodic stimulation current.

In another aspect, an embodiment of a method operative with a pulse generator for stimulating biological tissue is disclosed. The claimed embodiment comprises, inter alia, generating a programmable total stimulation current output for a stimulation pulse; simultaneously splitting the programmable total stimulation current output into a plurality of split current segments; and selectively mapping each of the split current segments to one or more electrodes of an implantable lead system comprising one or more leads, each having a plurality of electrodes, wherein an electrode of a select lead is operative, when activated, to apply a portion of the total stimulation current output for stimulating the biological tissue depending on an electrical connection relationship determined by a current mapping/routing control module. In one variation, an embodiment involves splitting the programmable total stimulation current output into equal fractions. In another variation, an embodiment involves splitting the programmable total stimulation current output into unequal fractions. The split current fractions, equal or otherwise, may be mapped to the selected electrodes (across one or more leads) either uniformly or by using a scaled/weighted distribution (e.g., binary-weighted distribution).

Additional/alternative features and variations of the embodiments will be apparent in view of the following description and accompanying Figures.

BRIEF DESCRIPTION OF THE DRAWINGS

Embodiments of the present disclosure are illustrated by way of example, and not by way of limitation, in the Figures of the accompanying drawings in which like references indicate similar elements. It should be noted that different references to "an" or "one" embodiment in this disclosure are not necessarily to the same embodiment, and such references may mean at least one. Further, when a particular feature, structure, or characteristic is described in connection with an embodiment, it is submitted that it is within the knowledge of one skilled in the art to effectuate such feature, structure, or characteristic in connection with other embodiments whether or not explicitly described.

The accompanying drawings are incorporated into and form a part of the specification to illustrate one or more exemplary embodiments of the present disclosure. Various advantages and features of the disclosure will be understood from the following Detailed Description taken in connection with the appended claims and with reference to the attached drawing Figures in which:

DETAILED DESCRIPTION

Figure 1A:
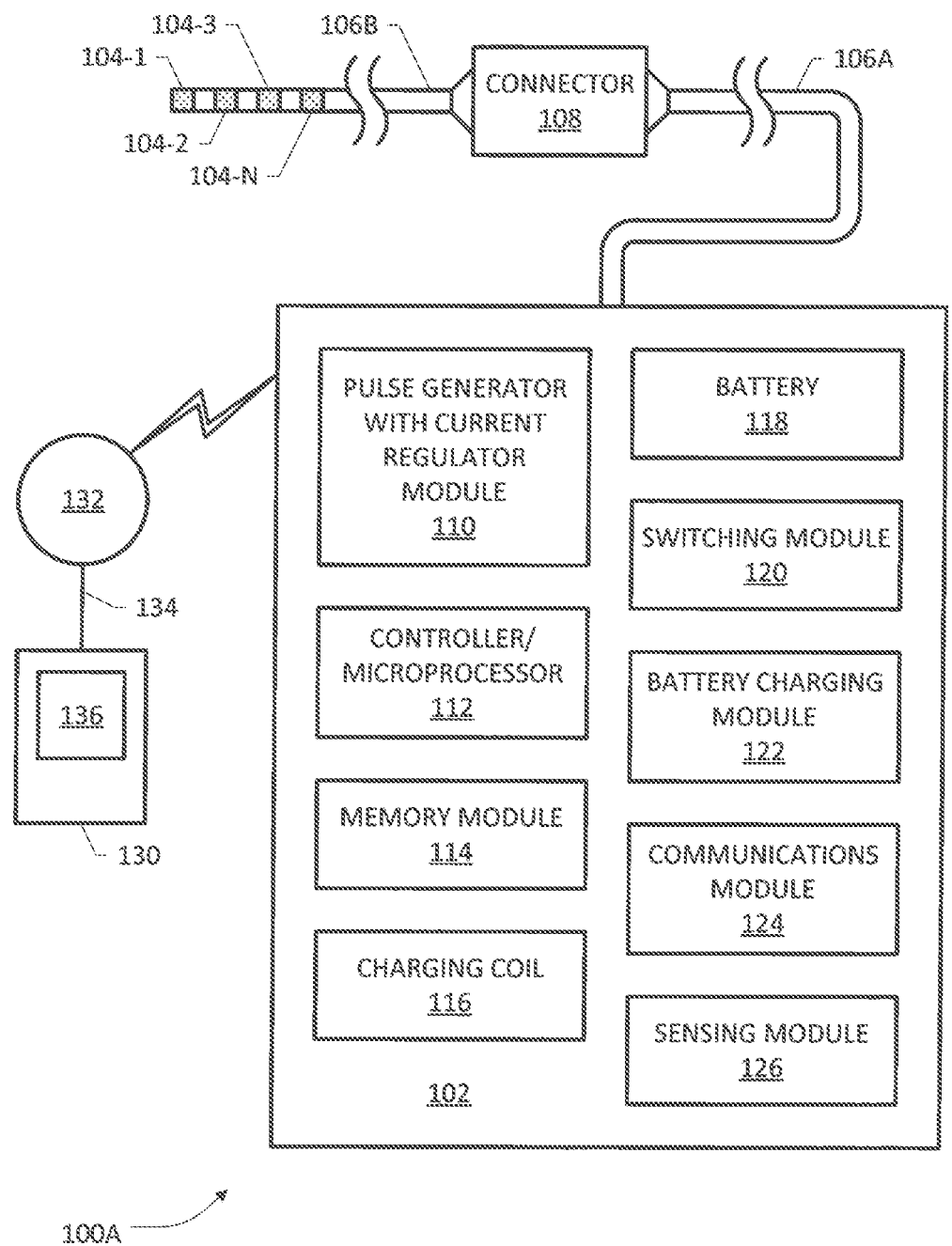
FIG. 1A depicts an example biostimulation system wherein one or more embodiments of a current regulator of the present disclosure may be practiced for effectuating stimulation current spitting in accordance with the teachings herein.

In the description herein for embodiments of the present disclosure, numerous specific details are provided, such as examples of circuits, devices, components and/or methods, to provide a thorough understanding of embodiments of the present disclosure. One skilled in the relevant art will recognize, however, that an embodiment of the disclosure can be practiced without one or more of the specific details, or with other apparatuses, systems, assemblies, methods, components, materials, parts, and/or the like. In other instances, well-known structures, materials, or operations are not specifically shown or described in detail to avoid obscuring aspects of embodiments of the present disclosure. Accordingly, it will be appreciated by one skilled in the art that the embodiments of the present disclosure may be practiced without such specific components. It should be further recognized that those of ordinary skill in the art, with the aid of the Detailed Description set forth herein and taking reference to the accompanying drawings, will be able to make and use one or more embodiments without undue experimentation.

Additionally, terms such as "coupled" and "connected," along with their derivatives, may be used in the following description, claims, or both. It should be understood that these terms are not necessarily intended as synonyms for each other. "Coupled" may be used to indicate that two or more elements, which may or may not be in direct physical or electrical contact with each other, co-operate or interact with each other. "Connected" may be used to indicate the establishment of communication, i.e., a communicative relationship, between two or more elements that are coupled with each other. Further, in one or more example embodiments set forth herein, generally speaking, an electrical element, component or module may be configured to perform a function if the element may be programmed for performing or otherwise structurally arranged to perform that function.

Some embodiments described herein may be particularly set forth with respect to an implantable pulse generator (IPG) for generating electrical stimulation for application to a desired area of a body or tissue based on a suitable stimulation therapy application, such as a spinal cord stimulation (SCS) system. However, it should be understood that example circuitry and methods of operation disclosed herein are not limited thereto, but have broad applicability, including but not limited to different types of implantable devices such as neuromuscular stimulators and sensors, dorsal root ganglion (DRG) stimulators, deep brain stimulators, cochlear stimulators, retinal implanters, drug delivery systems, muscle stimulators, tissue stimulators, cardiac stimulators, gastric stimulators, and the like, including other bioelectrical sensors and sensing systems, which may be broadly referred to as "biostimulation" applications and/or implantable medical devices (IMDs) for purposes of the present disclosure. Moreover, example circuitry and methods of operation disclosed herein are not limited to use with respect to an IPG or any particular form of IPG. For example, some embodiments may be implemented with respect to a fully implantable pulse generator, a radio frequency (RF) pulse generator, an external pulse generator, a micro-implantable pulse generator, inter alia.

Referring to FIG. 1A in particular, depicted therein is a biostimulation system 100A that generates electrical pulses for application to the target tissue of a patient wherein a stimulation current pulse may be simultaneously split into multiple current segments that may be individually applied to different electrodes according to one embodiment. By way of illustration, system 100A may be adapted to stimulate spinal cord tissue, peripheral nerve tissue, deep brain tissue, DRG tissue, cortical tissue, cardiac tissue, digestive tissue, pelvic floor tissue, or any other suitable biological tissue of interest within a patient's body, as noted above. System 100A includes an implantable pulse generator (IPG) 102 that is adapted to generate split stimulation current segments using a current regulator as will be set forth in additional detail hereinbelow. In one example embodiment, IPG 102 may be implemented as having a metallic housing or can that encloses a controller/processing block or module 112, pulse generating circuitry with current regulation module 110, a charging coil 116, a battery 118, a far-field and/or near field communication block or module 124, battery charging circuitry 122, switching circuitry 120, sensing circuitry 126, a memory module 114, and the like. Controller/processor module 112 typically includes a microcontroller or other suitable processor for controlling the various other components of the IPG device 102. Software/firmware code may be stored in memory 114 of IPG 102, which may be integrated with the controller/processor module 112, and/or other suitable application-specific storage components (not particularly shown in this FIG.) for execution by the microcontroller or processor 112 and/or other programmable logic blocks to control the various components of the device for purposes of an embodiment of the present patent disclosure.

In one arrangement, IPG 102 may be coupled to a separate or an attached extension component 106A for providing electrical and physical connectivity to a lead system 106B via a lead connector 108, wherein a distal end of the lead 106B includes a plurality of electrodes 104-1 to 104-N. Where the extension component 106A is provided as a separate component, the extension component 106A may connect with a "header" portion of IPG 102 as is known in the art. If the extension component 106A is integrated with IPG 102, internal electrical connections may be made through respective conductive components. Broadly, electrical pulses are generated by the pulse generating circuitry 110 under the control of processing block 112, and are provided to the switching circuitry 120 that is operative to selectively connect to electrical outputs of the IPG device, which are ultimately coupled to the electrodes 104-1 to 104-N at a distal end of the lead system 106B via respective electrical conductive traces.

In one arrangement, lead electrodes 104-1 to 104-N may be positioned along an axis of the lead 106B, with an angular offset such that the lead electrodes 104-1 to 104-N do not overlap. The lead electrodes 104-1 to 104-N may be in the shape of a ring such that each lead electrode continuously covers the circumference of the exterior surface of the lead 106B. Each of the lead electrodes 104-1 to 104-N are separated by non-conducting portions of the lead 106B, which electrically isolate each lead electrode 104-1 to 104-N from an adjacent lead electrode 104-1 to 104-N. The non-conducting portions of the lead 106B may include one or more insulative materials and/or biocompatible materials to allow the lead 106B to be implantable within the patient. Non-limiting examples of such materials include polyimide, polyetheretherketone (PEEK), polyethylene terephthalate (PET) film (also known as polyester or Mylar), polytetrafluoroethylene (PTFE) (e.g., Teflon), or parylene coating, polyether bloc amides, polyurethane, or the like compositions.

Additionally or alternatively, electrodes 104-1 to 104-N may be in the shape of a split or non-continuous ring such that the stimulation pulse(s) may be emitted in a manner so as to create an electric field emanating in an outward radial direction adjacent to the lead electrodes 104-1 to 104-N. Examples of lead electrodes 104-1 to 104-N and associated fabrication processes are disclosed in one or more of the following: (i) U.S. Patent Application Publication No. 2011/0072657, entitled, "METHOD OF FABRICATING STIMULATION LEAD FOR APPLYING ELECTRICAL STIMULATION TO TISSUE OF A PATIENT"; and (ii) U.S. Patent Application Publication No. 2018/0008821, entitled, "IMPLANTABLE THIN FILM DEVICES", each of which is incorporated herein by reference.

It should be noted the lead electrodes 104-1 to 104-N may be in various other formations, for example, in a planar formation, in an array or grid, etc. on a paddle structure as disclosed in U.S. Patent Application Publication No. 2014/0343564, entitled, "PADDLE LEADS FOR NEUROSTIMULATION AND METHOD OF DELIVERING THE SAME", which is incorporated herein by reference.

In one arrangement, the lead system 106B (as well as extension 106A where provided) may comprise a lead body of insulative material encapsulating a plurality of conductors within the material that extend from a proximal end (that is proximate to IPG 102) to the distal end of the lead body containing the lead electrodes 104-1 to 104-N. The conductors or conductive traces are operative to electrically couple the lead electrodes 104-1 to 104-N to a corresponding plurality of terminals (not shown) of the lead system 106A/B. In general, the terminals are adapted to receive electrical pulses from the pulse generation and switching circuitry of IPG 102, which are propagated via the corresponding conductive traces to at least a portion of the lead electrodes 104-1 to 104-N that are adapted to apply the pulses to a desired stimulation target of the patient depending on the particular stimulation therapy application. Also, sensing of physiological or bioelectrical signals may occur through the lead electrodes 104-1 to 104-N, corresponding conductors, and associated terminals. By way of illustration, an example embodiment of the stimulation system 100A may be provided with a plurality of lead electrodes 104-1 to 104-N comprising four electrodes, eight electrodes, etc., although any suitable number of electrodes (as well as corresponding conductive traces and terminals) may be provided in a lead system. Additionally or alternatively, various sensors (e.g., a position detector, temperature sensor, one or more electrochemical sensors, a radiopaque fiducial, etc.) may be located near the distal end of the lead 106B and electrically coupled to terminals through associated conductors within the lead body.

Although not required for all embodiments, the lead body of the implantable lead system 106A/106B may be fabricated to flex and elongate upon implantation or advancing within or relative to the tissue (e.g., nervous tissue) of the patient towards the stimulation target to account for movement of the patient during or after implantation. Fabrication techniques and material characteristics for "body compliant" leads are disclosed in greater detail in U.S. Pat. No. 9,844, 661, entitled "COMPLIANT ELECTRICAL STIMULATION LEADS AND METHODS OF FABRICATION", which is incorporated herein by reference.

An example implementation of the components within IPG 102, such as, e.g., processor and associated charge control circuitry for an IPG, is described in U.S. Pat. No. 7,571,007, entitled "SYSTEMS AND METHODS FOR USE IN PULSE GENERATION", which is incorporated herein by reference. An example implementation of circuitry for recharging a rechargeable battery (e.g., battery charging circuitry 122) of an IPG using inductive coupling and external charging circuits is described in U.S. Pat. No. 7,212,110, entitled "IMPLANTABLE DEVICE AND SYSTEM FOR WIRELESS COMMUNICATION", which is incorporated herein by reference. Still further, an example implementation of "constant current" pulse generating circuitry (e.g., at least a portion of pulse generating circuitry 110) is provided in U.S. Patent Application Publication No. 2006/0170486 entitled "PULSE GENERATOR HAVING AN EFFICIENT FRACTIONAL VOLTAGE CONVERTER AND METHOD OF USE", which is incorporated herein by reference. One or multiple sets of such circuitry may be provided within IPG 102 operating in association with a current regulator according to the teachings of the present disclosure for splitting a stimulation current pulse across a select number of electrodes (across one or more implantable leads) as will be set forth in additional detail further below. Different stimulation pulses on different lead electrodes selected from electrodes 104-1 to 104-N may be generated using consecutively generated pulses according to a "multi-stimset program" as is known in the art. Complex pulse parameters may be employed such as those described in U.S. Pat. No. 7,228,179, entitled "METHOD AND APPARATUS FOR PROVIDING COMPLEX TISSUE STIMULATION PATTERNS", and International Patent Publication Number WO 2001/093953, entitled "NEUROMODULATION THERAPY SYSTEM", which are incorporated herein by reference. Alternatively, multiple sets of such stimulation circuitry may be employed to provide high frequency pulse patterns (e.g., tonic stimulation waveform, burst stimulation waveform, and the like) that include generated and delivered stimulation therapy through one or more leads or electrodes 104-1 to 104-N as is also known in the art. Various sets of parameters may define the pulse characteristics and pulse timing for the pulses applied to the various lead electrodes as is known in the art. Although constant current pulse generating circuitry is contemplated for some embodiments, any other suitable type of pulse generating circuitry may be employed such as constant voltage pulse generating circuitry.

In an example implementation of IPG 102, sensing circuitry 126 may be optionally provided, preferably adapted to measure a suitable electric parameter or transduced characteristic (e.g., voltage, current, capacitance, etc.) over a configurable time associated with the stimulation target or tissue through at least one of the electrodes proximate to the stimulation target. For example, the sensing circuitry 126 may measure an evoked compound activation potential (ECAP) waveform from an Aβ sensory fiber or spinal cord. Optionally, the sensing circuitry 126 may store the measured/sensed electric data in memory 114.

An external device 130 may be implemented to charge/recharge the battery 118 of IPG 102 (although a separate recharging device could alternatively be employed), to access memory 114, and/or to program or reprogram IPG 102 with respect to the stimulation set parameters including pulsing specifications while implanted within the patient. In alternative embodiments, however, separate programmer devices may be employed for charging and/or programming the IPG 102 device and/or any programmable components thereof. An example embodiment of the external device 130 may be a processor-based system that possesses wireline and/or wireless communication capabilities, e.g., a tablet, smartphone, laptop computer, handheld computer, a personal digital assistant (PDA), or any smart wearable device and smart digital assistant device, etc. Software may be stored within a non-transitory memory of the external device 130, which may be executed by the processor to control the various operations of the external device 130. A connector or "wand" 134 may be electrically coupled to the external device 130 through suitable electrical connectors (not specifically shown), which may be electrically connected to a telemetry component 132 (e.g., inductor coil, RF transceiver, etc.) at the distal end of wand 134 through respective communication links that allow bi-directional communication with IPG 102. Optionally, in some embodiments, the wand 134 may comprise one or more temperature sensors for use during charging operations.

In general operation, a user (e.g., a doctor, a medical technician, or the patient) may initiate communication with IPG 102 by placing the wand 134 proximate to the stimulation system 100A. Preferably, the placement of the wand 134 allows the telemetry system to be aligned with the far-field and/or near field communication circuitry 124 of IPG 102. The external device 130 preferably provides one or more user interfaces 136 (e.g., touch screen, keyboard, mouse, buttons, scroll wheels or rollers, or the like), allowing the user to operate IPG 102. The external device 130 may be controlled by the user through the user interface 136, allowing the user to interact with IPG 102, including, e.g., effectuating programmatic control for dynamically configuring stimulation current splits as will be set forth further below. Further, the user interface 136 may permit the user to move electrical stimulation along and/or across one or more of the lead(s) 106A using different lead electrode combinations selected from electrodes 104-1 to 104-N, for example, as described in U.S. Patent Application Publication No. 2009/0326608, entitled "METHOD OF ELECTRICALLY STIMULATING TISSUE OF A PATIENT BY SHIFTING A LOCUS OF STIMULATION AND SYSTEM EMPLOYING THE SAME", which is incorporated herein by reference. Optionally, the user interface 136 may permit the user to designate which electrodes 104-1 to 104-N are to stimulate (e.g., emit current pulses, in an anode state, in a cathode state), or not selected to stimulate (i.e., remain inactive or floating), with respect to a potential stimulation target, to measure/sense tissue electrical parameters, or the like. Additionally or alternatively, the external device 130 may access or download the electrical measurements from the memory 114 acquired by the sensing circuitry 126.

In some implementations, the external device 130 may permit operation of IPG 102 according to one or more spinal cord stimulation (SCS) programs or therapy applications to treat the patient. Each SCS program may include one or more sets of stimulation parameters of the pulse including pulse amplitude, stimulation level, pulse width, pulse frequency or inter-pulse period, pulse repetition parameter (e.g., number of times for a given pulse to be repeated for respective stimulation sets or stimsets during execution of program), biphasic pulses, monophasic pulses, etc. IPG 102 modifies its internal parameters in response to the control signals from the external device 130 to vary the stimulation characteristics of the stimulation therapy transmitted through the lead system 106A/106B to the tissue of the patient. Example neurostimulation (NS) systems, stimsets, and multi-stimset programs are set forth in U.S. Pat. No. 7,228,179, entitled "METHOD AND APPARATUS FOR PROVIDING COMPLEX TISSUE STIMULATION PATTERNS", and International Patent Publication Number WO 2001/093953, entitled "NEUROMODULATION THERAPY SYSTEM", which are incorporated hereinabove by reference.

Figure 1B:
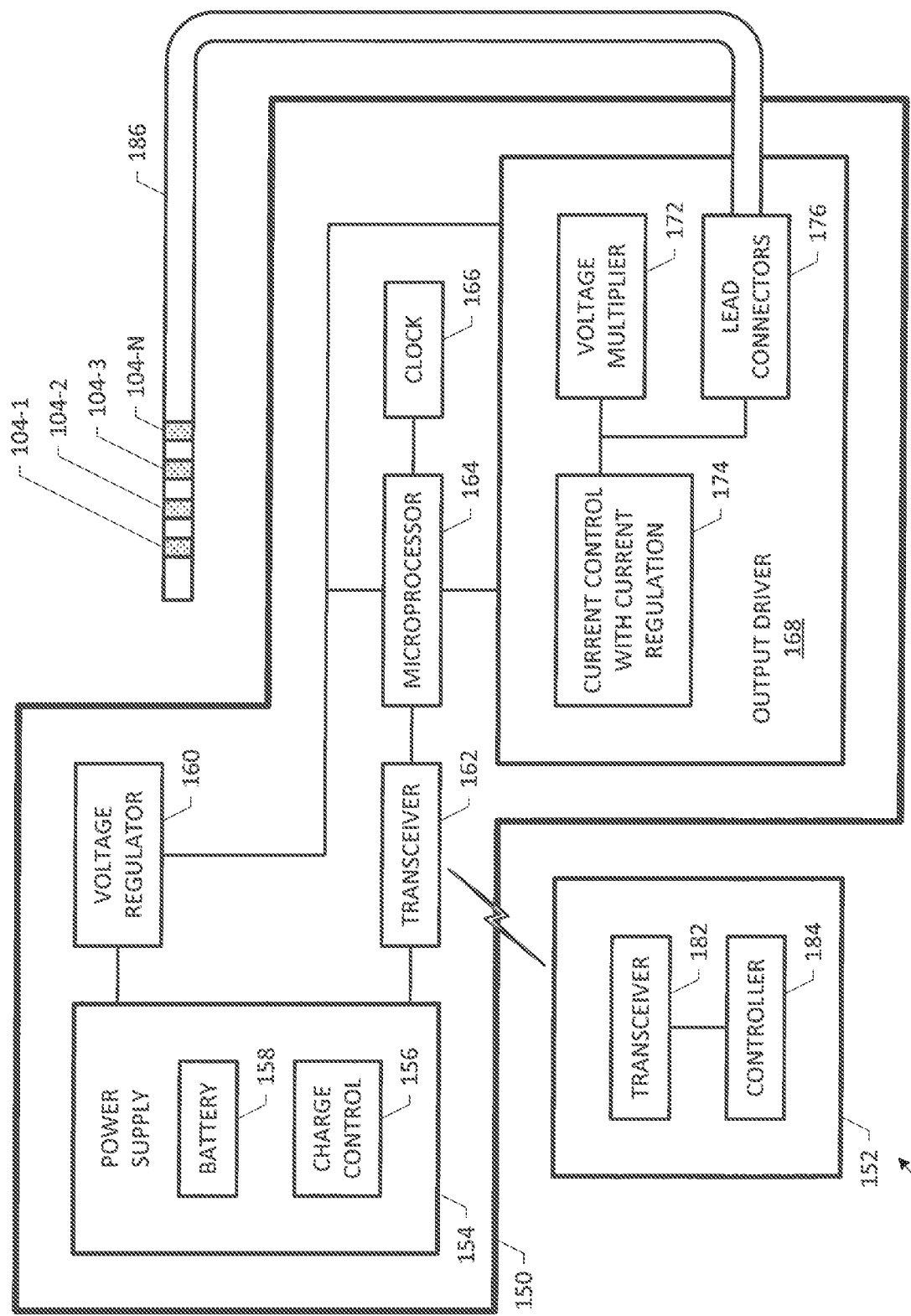
FIG. 1B depicts another view of a biostimulation system that illustrates additional details of a pulse generator configured to include a current regulator according to an embodiment of the present disclosure.

FIG. 1B depicts another embodiment of a biostimulation system 100B that illustrates additional details of a pulse generator 150 configured to include a current regulator according to an embodiment of the present disclosure. Stimulation system 100B is adapted to include a generator portion, shown as IPG 150, providing a stimulation or energy source, a stimulation portion, shown as lead system 186 for application of the stimulus pulse(s) similar to the lead system 106A/B described above, and an optional external controller, shown as programmer/controller 152, to program and/or control IPG 150 via a wired/wireless communications link, similar to the external device 130 described in the foregoing sections. IPG 150 may be implanted within the body of a human or animal patient (not shown) for providing electrical stimulation from IPG 150 to a selected area of the body via lead 186 under control of external programmer/controller 152. It should be appreciated that although lead 186 is illustrated to provide a stimulation portion of stimulation system 100B configured provide stimulation remotely with respect to the generator portion 150 of stimulation system 100B, a lead as described herein is intended to encompass a variety of stimulation portion configurations including, e.g., a microstimulator electrode disposed adjacent to a generator portion.

Furthermore, one skilled in the art will recognize that although example lead systems 186 and 106A/B shown in FIGS. 1A/1B are exemplified with a single implantable lead, the teachings herein are not necessarily limited thereto and an example embodiment of the present invention may involve a lead system comprising two or more implantable leads, with each lead having a plurality of electrodes, wherein different electrodes may be grouped into different channels in a stimulation application and a stimulation current may be split and mapped across a number of electrodes regardless of the channels or whether one or more leads are selected for stimulation.

IPG 150 may comprise a self-contained implantable pulse generator having an implanted power source such as a long-lasting or rechargeable battery. Alternatively, IPG 150 may comprise an externally-powered implantable pulse generator receiving at least some of the required operating power from an external power transmitter, preferably in the form of a wireless signal, which may be radio frequency (RF)-based, via inductive coupling, etc., as noted previously. IPG 150 of the illustrated embodiment includes a voltage regulator 160, power supply 154, transceiver 162, microcontroller (or microprocessor) 164, clock 166, and output driver circuitry 168 comprising a current regulator block 174, which will be described in further detail below. Power supply 154 provides a source of power, such as from battery 158 (which may comprise a non-rechargeable battery, e.g., single use battery, a rechargeable battery, a capacitor, and/or like power sources), to other components of IPG 150, as may be regulated by voltage regulator 160 including and/or facilitating digitally-programmable analog voltage generation. Charge control 156 of an example embodiment of IPG 150 is operative to provide management with respect to battery 158. Transceiver 162 of an example embodiment of IPG 150 is operative to provide data/control communication between microprocessor 164 and a controller 184 of external programmer/controller 152, via transceiver 182 provided therewith. Transceiver 162 of an example embodiment, in addition to or in the alternative to providing data/control communication, may provide a conduit for delivering energy to power supply 158 via RF or inductive recharging as set forth above.

Microprocessor/controller 164 provides overall control with respect to the operation of IPG 150, such as in accordance with a program stored therein or provided thereto by external programmer/controller 152. Output driver circuitry 168 may be configured to generate and deliver current pulses that are simultaneously split into multiple current segments of configurably varying current amounts to selected ones of electrodes 104-1 to 104-N under control of microcontroller 164. In general operation, for example, a voltage multiplier 172 and current control 174 may be controlled to deliver a constant current pulse of a desired magnitude, duration, and frequency to a tissue load present with respect to particular ones of electrodes 104-1 to 104-N. Clock 166 preferably provides system timing information, such as may be used by microcontroller 164 in controlling system operation, as may be used by voltage multiplier 172 in generating a desired voltage, etc.

Lead system 186 of the illustrated embodiment includes a lead body encapsulating a plurality of internal conductors coupled to lead connectors (not shown) to interface with lead connectors 176 of IPG 150 in a hermetically sealed arrangement. The internal conductors provide electrical connection from individual lead connectors to each of a corresponding one of electrodes 104-1 to 104-N, which may be configured to provide anodic current stimulation and/or cathodic current stimulation for application at, or proximate to, a spinal nerve or peripheral nerve, brain tissue, muscle, or other tissue depending on a desired therapy. IPG 150 may be configured to control the electrical signals by varying signal parameters such as intensity, duration and/or frequency in order to deliver a desired therapy and/or otherwise provide stimulation current splitting operations as described herein.

Skilled artisans will recognize that any number of electrodes, and corresponding conductors, may be utilized according to some embodiments, as previously noted. Moreover, various types, configurations and shapes of electrodes (and lead connectors) may be used according to some embodiments. An optional lumen (not shown) may extend through the lead 186, such as for use in delivery of chemicals or drugs or to accept a stylet during placement of the lead within the body of a patient. Additionally or alternatively, the lead (stimulation portion) and IPG (generator portion) may comprise a unitary construction, such as that of a microstimulator configuration.

As mentioned above, programmer/controller 152 of an example embodiment provides data communication with IPG 150, such as to provide control (e.g., adjust stimulation settings), provide programming (e.g., selection and/or electrical polarity configuration of the electrodes to which stimulation pulses are delivered), etc. In addition, programmer/controller 152 of an example embodiment may be configured to provide current splitting parameters to facilitate simultaneous splitting of stimulation current of a stimulation pulse to generate multiple split current segments having configurable fractions of a total stimulation current output programmed for a pulse. An embodiment of a pulse generation system and the delivery of stimulation pulses that may be configured to interoperate with the teachings herein may be found in U.S. Pat. No. 6,609,031, entitled "MULTIPROGRAMMABLE TISSUE STIMULATOR AND METHOD", which is hereby incorporated herein by reference.

In one example embodiment of IPG 150, voltage regulator 160 may be configured to accept a reference voltage $V_{REF}$, which may be prone to variation in magnitude, and provide an output voltage $V_{OUT}$ having a selected, relatively constant magnitude. For example, $V_{REF}$ may be provided by battery 158 which may have a relatively high voltage when initially charged or put into service and the voltage may drop over the life or charge cycle of the battery. However, circuitry of IPG 150 may malfunction if a voltage applied thereto is not within particular limits, and the high and low voltage extremes associated with battery 158 may be outside of these limits in some instances. Accordingly, voltage regulator 160 may be configured to regulate $V_{REF}$ as provided by battery 158 to provide a regulated supply $V_{OUT}$ within a range acceptable to circuitry of IPG 150, including output driver circuitry 168 having current control and regulation 174 for purposes of an example embodiment of the present disclosure.

In general operation, a typical voltage regulator is capable of maintaining an output voltage only when the reference voltage provided thereto is at least slightly higher than the output voltage. However, over the course of a battery's life or charge cycle, the voltage provided thereby may be reduced to a point too near or below the $V_{OUT}$, causing the voltage regulator output voltage to also fall. In such a situation, therefore, the regulator can no longer provide the desired regulated output voltage. However, voltage regulator 160 of the illustrated embodiment is adapted to provide a desired output voltage level even when a reference voltage provided by battery 158 drops below the desired output voltage.

In one example implementation, voltage regulator 160 may include a multiplexer having multiple voltage inputs that are at different levels of the battery voltage ($V_B$), which may be selected under programmatic control to provide a suitable voltage supply output for the components of IPG 150. Some embodiments may also implement a closed loop control system with respect to voltage regulator 160 in order to provide further voltage selection control in association with suitable control signaling. For example, sensing circuitry, such as may utilize an analog-to-digital converter (ADC) in making voltage measurements may be utilized according to a preferred embodiment to provide information with respect to the battery voltage, which may be used by a digital control system (e.g., supported by microcontroller 164) in order to provide appropriate control signals e.g., select signals, for controlling the output voltage of voltage regulator 160. Additional details regarding voltage regulation may be found in U.S. Patent Application Publication No. 2009/0048643, entitled "METHOD FOR PROVIDING MULTIPLE VOLTAGE LEVELS DURING PULSE GENERATION AND IMPLANTABLE PULSE GENERATING EMPLOYING THE SAME" (hereinafter "the '643 patent application publication"), which is hereby incorporated herein by reference.

Skilled artisans will recognize that although an embodiment of voltage regulation is set forth hereinabove, a variety of techniques and circuits may be provided for operation with a current regulator scheme described below in a particular implementation. Broadly, any suitable voltage regulator/multiplier arrangement may be adapted to provide dynamic voltage adjustment, which may be operative with a digitally-programmable analog voltage generator for providing a voltage level that may be used for generating a desired stimulation current level and splitting it into multiple split current segments for selective electrode stimulation in an example embodiment of the present disclosure.

Figure 2:
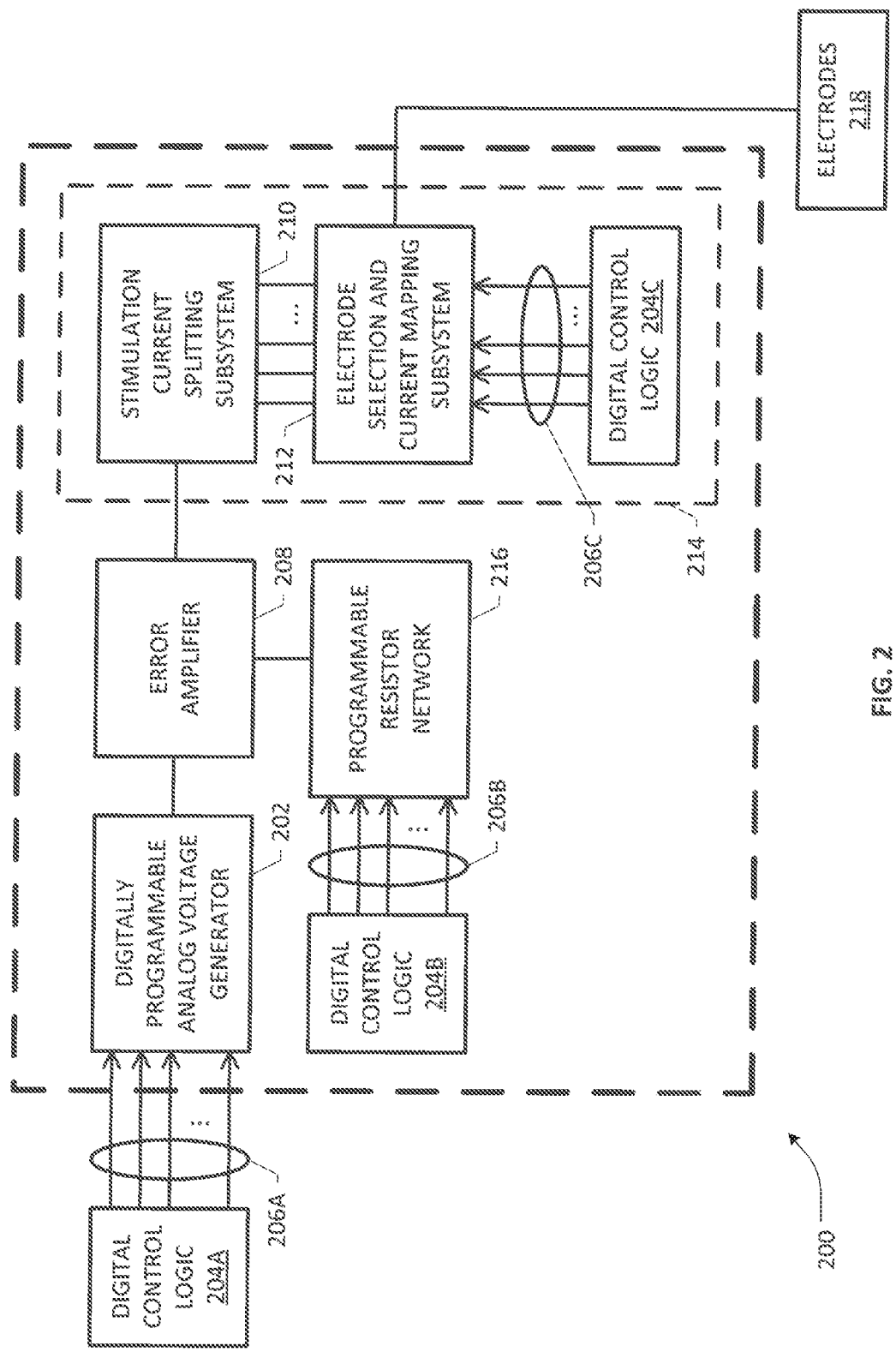
FIG. 2 depicts a block diagram of a current regulator according to an embodiment of the present disclosure.

FIG. 2 depicts a block diagram of a current regulator 200 according to an embodiment of the present disclosure wherein various digital control signals may be generated from one or more sources of an IPG and/or associated external programmer device arrangement to effectuate a current splitting scheme for achieving a more optimal electric field distribution at or near a biostimulation target. A digitally programmable analog voltage generator 202, which may be configured to interoperate and/or integrate with any suitable voltage regulator such as described above, may be configured to generate a desired output voltage responsive to one or more control signals 206A from a digital control logic module 204A. An error amplifier 208 may be coupled to the voltage generator 202 to accept the output voltage therefrom and controllably generate a total stimulation current output responsive to a programmable resistor network 216, which in turn may be controlled by one or more control signals 206B from a digital control logic module 204B. As will be seen below, the programmable resistor network 216 may be dynamically adjusted to specify a particular total stimulation current setting depending on the therapy application (or a modification thereof), which can be reliably produced and applied to a set of selected electrodes 218 (across one or more implantable leads) regardless of variations in the load resistance of a stimulation target tissue because of a feedback control loop arrangement provided with respect to the error amplifier 208. In accordance with the teachings herein, a current splitting and mapping mechanism 214 is operative to simultaneously split the particular total stimulation current into a plurality of split current segments based on a splitting circuitry mechanism 210, which may be coupled to a current segment mapping mechanism 212 configured to electrically route or map the individual split current segments to selected electrodes depending on appropriate control signals 206C provided from a suitable digital control logic module 204C.

Figure 3:
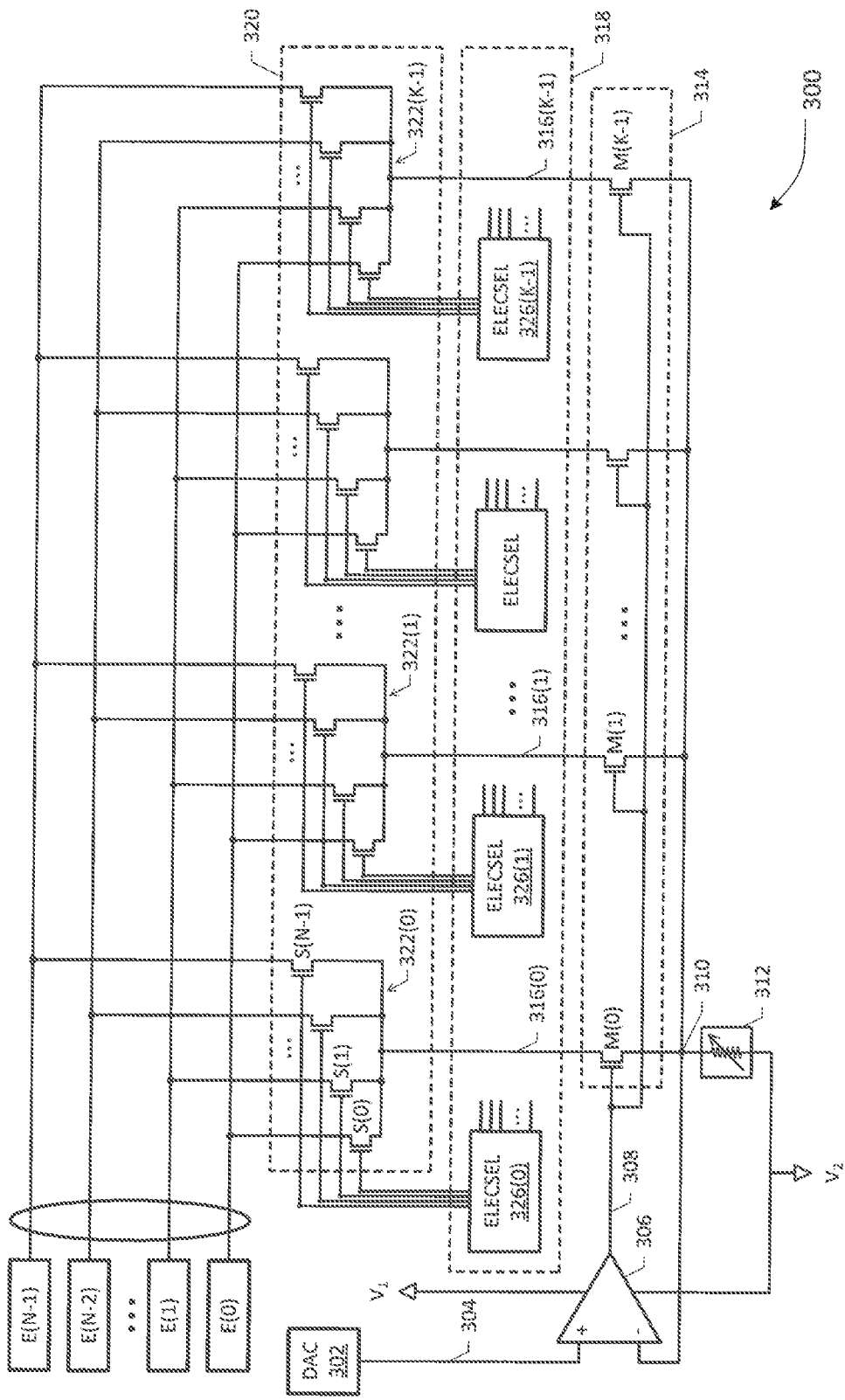
FIG. 3 depicts a circuit diagram of a current regulator according to an embodiment of the present disclosure.

FIG. 3 depicts a circuit diagram of a current regulator 300 with additional details according to an embodiment of the present disclosure. By way of illustration, a digital-to-analog converter (DAC) 302 may be provided to interface with appropriate voltage supply (e.g., having suitable magnitude and polarity, depending on the type of stimulation current being programmed) to generate a digitally-programmed analog voltage level as an output signal 304, which may be provided to an error amplifier 306. In one arrangement, the error amplifier 306 may be implemented as an op amp having two inputs for providing a differential input and operative with a pair of power supply voltage nodes, $V_1$ and $V_2$, that may be suitably biased depending on whether cathodic stimulation current or anodic stimulation current is being programmed. Accordingly, the digitally-programmed analog voltage signal (VDAC) 304 may be coupled to a first input of the error amplifier 306, wherein a second input is coupled to a programmable resistor network 312 operative to provide a digitally-programmed resistance (RSCALE) in a feedback loop arrangement for modulating a current output. In general operation, the error amplifier 306 may be programmatically configured to generate a desired amount of total stimulation current (IOUT), which may be set by the application of Ohm's Law in view of the digitally-programmed resistance RSCALE, where IOUT=(VDAC/RSCALE), at a node 310 to which the programmable resistor network 312 is connected.

A plurality of current splitting switches M(0) to M(K−1) coupled to the output node 310 may be configured to operate as a current splitting switch subsystem 314 for splitting the total stimulation current output (IOUT) available at output node 310 into a corresponding number of current segments 316(0) to 316(K−1), each having a split current amount ISPLIT(0) to ISPLIT(K−1), wherein Σ{ISPLIT(i)}=IOUT, i=0, 1, . . . , (K−1). A common control signal generated by the error amplifier 306 as a voltage signal at an output node 308 may be used to enable or disable each of the current splitting switches, M(0) to M(K−1) during a stimulation pulse event. Skilled artisans will recognize upon reference hereto that the current splitting switches, M(0) to M(K−1) may be implemented using a variety of switching devices known in the electrical arts, e.g., including but not limited to bipolar junction transistors (BJTs), metal oxide semiconductor field effect transistors (MOSFETS), junction gate FETs (JFETs), n-channel MOSFET (NMOS) devices, p-channel MOSFET (PMOS) devices, depletion-mode or enhancement-mode devices, and the like, as well as any digital logic gates built therefrom. It will be further understood that the sizing (e.g., channel width and length) and biasing of the switching devices is highly configurable, e.g., depending on whether anodic current stimulation or cathodic stimulation current is being programmed (i.e., whether the electrodes of a lead system are configured to operate as current sink terminals or cathodes, or as current source terminals or anodes) as well as how much current is to be carried on each split current segment (i.e., granularity and distribution of the split current segments resulting from simultaneously splitting the total stimulation current output, IOUT).

In one arrangement, the current splitting switch subsystem 314 comprising current splitting switches M(0) to M(K−1) may be configured to split IOUT into equal fractions, IOUT/K, by sizing the K switches in an identical manner. A different number and/or distribution of current fractions may be implemented in additional or alternative embodiments, e.g., with non-uniform or unequal scaling that result into linear/nonlinear weighted distributions (e.g., binary-weighted), and the like, wherein differently sized switching devices and/or other arrangements of the switching devices may be utilized as will be apparent to one skilled in the art.

In one arrangement, the plurality of split current segments 316(0) to 316(K−1) are provided to a current mapping/routing module 320 comprising a corresponding number of mapping element banks 322(0) to 322(K−1) that may be programmatically configured to select at least a portion of electrodes E(0) to E(N−1) (which may be selected from one or more implantable leads) and switchably connect each split current segment thereto. Preferably, each bank of mapping elements 322(0) to 322(K−1) may comprise N pass gates corresponding to N electrodes (E(0) to E(N−1)), which may be implemented using a variety of switching devices known in the electrical arts as noted hereinabove. In one arrangement, each bank of mapping elements may be controlled by a corresponding electrode select logic module which may be implemented using suitable digital logic circuitry configured to decode an m-bit wide control signal provided by and/or generated from an IPG or associated external programmer device (shown in FIGS. 1A and 1B). By way of illustration, electrode select (ELECSEL) logic modules 326(0) to 326(K−1) may form a "decode" block 318 coupled to the plurality of split current segments 316(0) to 316(K−1), wherein each electrode select logic module 326($i$), i=0, 2, . . . , (K−1), receives a digital control signal of $\log_2\{N\}$ bits, N=the number of electrodes, which may be decoded to assert or enable a single control signal to activate a particular pass gate for mapping the corresponding split current segment to a single one of the electrodes. In other words, each split current segment 316($i$), i=0, 2, . . . , (K−1), can be individually coupled to any one of the N electrodes (e.g., spread across one or more implantable leads) based on programmatic control in order to achieve a myriad of combinations of split current combinations that may be applied to a biostimulation target tissue. Further, because any subset of the N electrodes may be selected for providing stimulation via one or more leads, a variety of spatial patterns may be obtained depending on the electrode configuration in order to effectuate a plurality of electric field distributions applied to the biostimulation target tissue with increased granularity, modulation, and a greater degree of control for a particular therapy application. By way of illustration, if eight electrodes are provided in a single-lead system, out of which two spatially separated electrodes comprising a most distal electrode E(7) and a least distal electrode E(0) are selected for stimulation with a total stimulation current of 8 milliamps (mA) in a pulse of 5 microseconds (µs), a current regulator embodiment involving eight-way equal fraction current splitting may be configured such that any four split current segments each having 1 mA may be synchronously, e.g., simultaneously, mapped to E(0) while the remaining four split current segments totaling 4 mA may likewise synchronously/simultaneously be mapped to E(7) for the pulse width duration. Likewise, the total stimulation current of 8 mA may be split in an eight-way equal fraction and mapped to different electrodes of different leads in an example embodiment. For instance, in a lead system having four leads, each lead having four electrodes, an embodiment of the present disclosure may be configured such that any two electrodes from each lead may be selected wherein each electrode receives a 1 mA split stimulation current according to an embodiment of the present disclosure.

In one exemplary implementation, any of the N electrodes (across one or more leads) may be assigned to a select number of "channels" (e.g., two-channel, four-channel, eight-channel, etc.), with the number of electrodes per channel being configurable under programmatic control of the IPG and/or associated external programmer device. Typically, the channel identifies which electrodes are selected to synchronously source or sink current to create an electric field in the tissue to be stimulated (i.e., anodic current stimulation or cathodic current stimulation). Amplitudes and polarities of the electrodes on a channel may vary, e.g., as may be controlled by manipulating the program software settings. For instance, such programming software or firmware may be manipulated to set a number of parameters including but not limited to electrode polarity, amplitude, pulse rate/frequency and pulse width for the electrodes of a given channel, and the like.

Accordingly, the N programmable electrodes can be programmed to have a positive polarity (sourcing current), a negative polarity (sinking current), or no polarity (i.e., no current) in any of the channels. Additionally, each of the N electrodes can operate in a bipolar mode or multipolar mode, e.g., where two or more electrode contacts are grouped to source/sink current at the same time. Alternatively, each of the N electrodes can operate in a monopolar mode where, for example, the electrode contacts associated with a channel may be configured as cathodes or negative terminals, and the case electrode (i.e., the IPG case or housing) may be configured as an anode or positive terminal, or vice versa, with the understanding that the direction in which current flows is a relative concept, and different conventions can be used to define whether currents flow to or from various sources/sinks.

Skilled artisans will therefore recognize that an embodiment of current regulator 300 may be implemented either in a cathodic stimulation current splitting application or an anodic stimulation current splitting application with relevant modifications provided accordingly, mutatis mutandis. For example, where cathodic stimulation is provided, NMOS devices having appropriate sizes and voltage biasing may be used in an implementation of the current regulator. On the other hand, PMOS devices with appropriate sizing and voltage biasing (essentially reversing the polarities used in an NMOS Implementation) may be used for anodic stimulation. As the magnitude of anodic currents may be greater than typical cathodic currents in an implementation, larger devices may be required for current regulation and anodic stimulation current splitting in an example embodiment.

Figure 4:
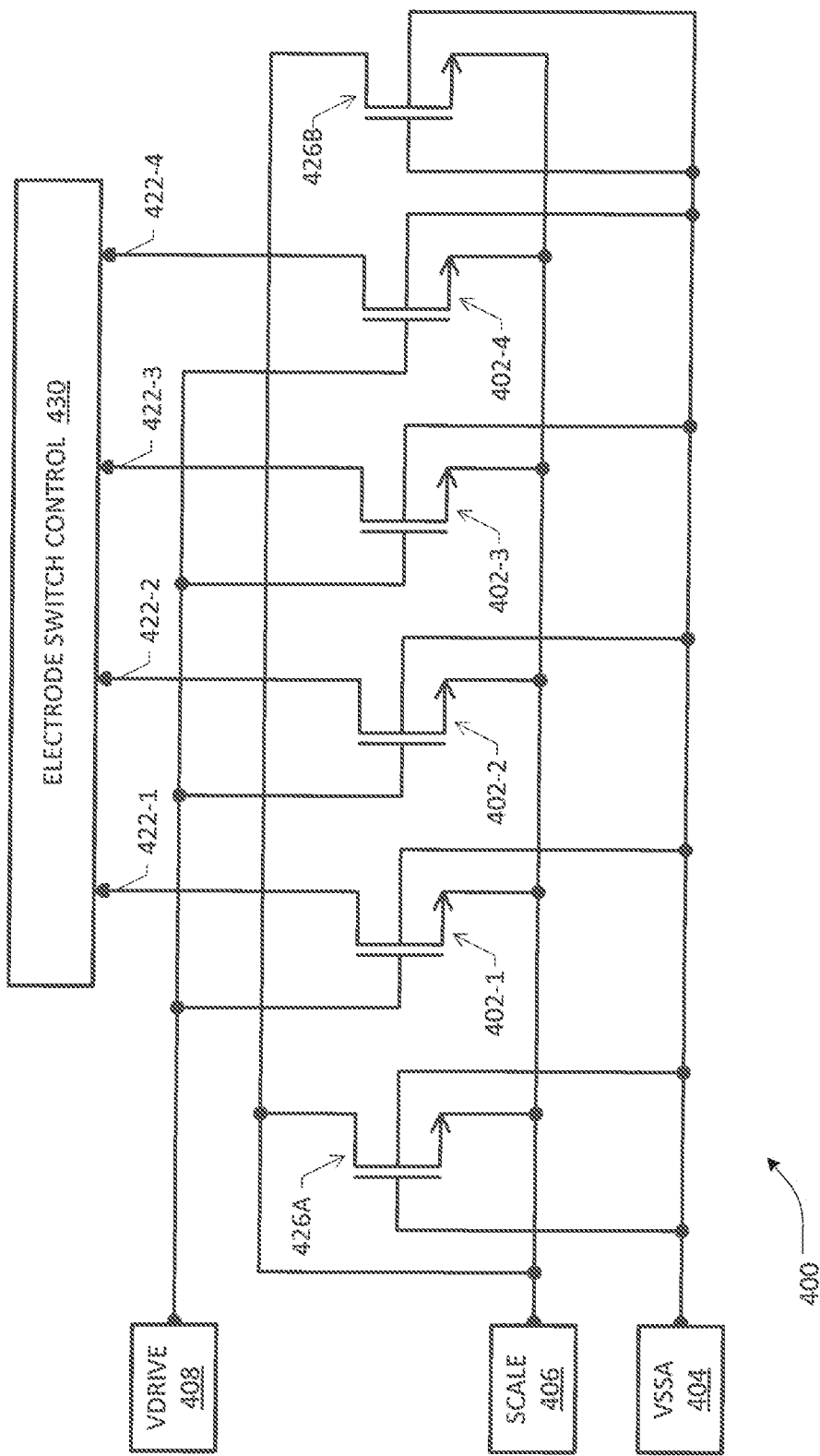
FIG. 4 depicts an example current splitting circuit that illustrates additional details according to an embodiment of the present disclosure.

Turning to FIG. 4, an example stimulation current splitting circuit 400 involving an NMOS implementation is illustrated with additional details according to an embodiment of the present disclosure. Four identical NMOS devices 402-1 to 402-4 are operative as current splitting switches whose body or substrate is biased to a voltage VSSA 404, with respective drains coupled to corresponding split current segments 422-1 to 422-4 and respective sources commonly coupled to a SCALE node 406 that is supplied a programmable total stimulation current output as set forth above. A VDRIVE node 408 is commonly coupled to each gate of the current splitting NMOS devices 402-1 to 402-4 for turning on the devices when a gate control voltage, VDRIVE 408, is provided by the error amplifier output (e.g., node 308 in FIG. 3). A pair of matching "dummy" NMOS devices 426A and 426B may be provided for electrically matching the current splitting devices and ensuring that the total stimulation current is evenly split at 25% during a stimulation pulse. As described in detail hereinabove, the split current segments 422-1 to 422-4 each carrying 25% of the total programmed stimulation current may be provided to an electrode switch control block 430 for electrode selection and current mapping under programmatic control.

Additional and/or alternative arrangements wherein an embodiment of a current regulator configured to provide simultaneously split current segments according to the teachings of the present patent disclosure are set forth in the following sections. As noted previously, example embodiments of IPG 102/150 may be housed within a hermetically sealed container having at least a portion of which is electrically conductive. Such a housing may comprise a metal "can" or "case" surrounding components of the IPG, wherein the electrically conductive portion of the housing may be electrically coupled to output driver circuitry 168 (shown in FIG. 1B) so as to allow the use of housing as an electrode during delivery of pulses. The use of an IPG's housing as an electrode, particularly as an anode, facilitates the use of a monopole electrode configuration with respect to a lead subsystem, e.g., lead subsystem 186, which may be particularly beneficial in therapy applications such as deep brain stimulation or other desirable tissue stimulation situations.

In a still further arrangement, an IPG's housing may be selectable as an anode, a cathode, or disconnected from the delivery of a pulse. Accordingly, such a housing may be utilized in an active discharge pulse delivery scheme. For example, a housing may be configured as an anode during a stimulation pulse and then reconfigured as a cathode during a corresponding active discharge pulse. Such a configuration may facilitate increased frequency and/or amplitude monopole stimulation with respect to the lead electrodes selected to receive the split stimulation current according to example embodiments of the present patent disclosure.

Some embodiments may be configured to provide programming to restrict configuring an IPG's housing as a cathode with respect to particular pulses, such as the aforementioned active discharge pulse. For example, it may be desired to prevent configuration of an IPG's housing as a cathode during a stimulation pulse so as to prevent stimulation of tissue surrounding the IPG housing. Accordingly, in some embodiments of the present patent disclosure, suitable control systems, including microcontroller 112/164 (shown in FIGS. 1A/1B), are operative to automatically configure an IPG's housing as a cathode at an appropriate time, so as to provide active discharge for monopole stimulation where, due to stimulation frequency and/or stimulation amplitude, charge may have accumulated over the electrode blocking capacitors typically provided in an implementation. Accordingly, it should be appreciated that electrical configuration of a housing as a cathode according to some embodiments is circuit determinable. Additional details regarding configuring lead electrodes as cathodes or anodes, either during stimulation or for discharging, may be found in the '643 patent application publication incorporated by reference hereinabove.

Figure 5:
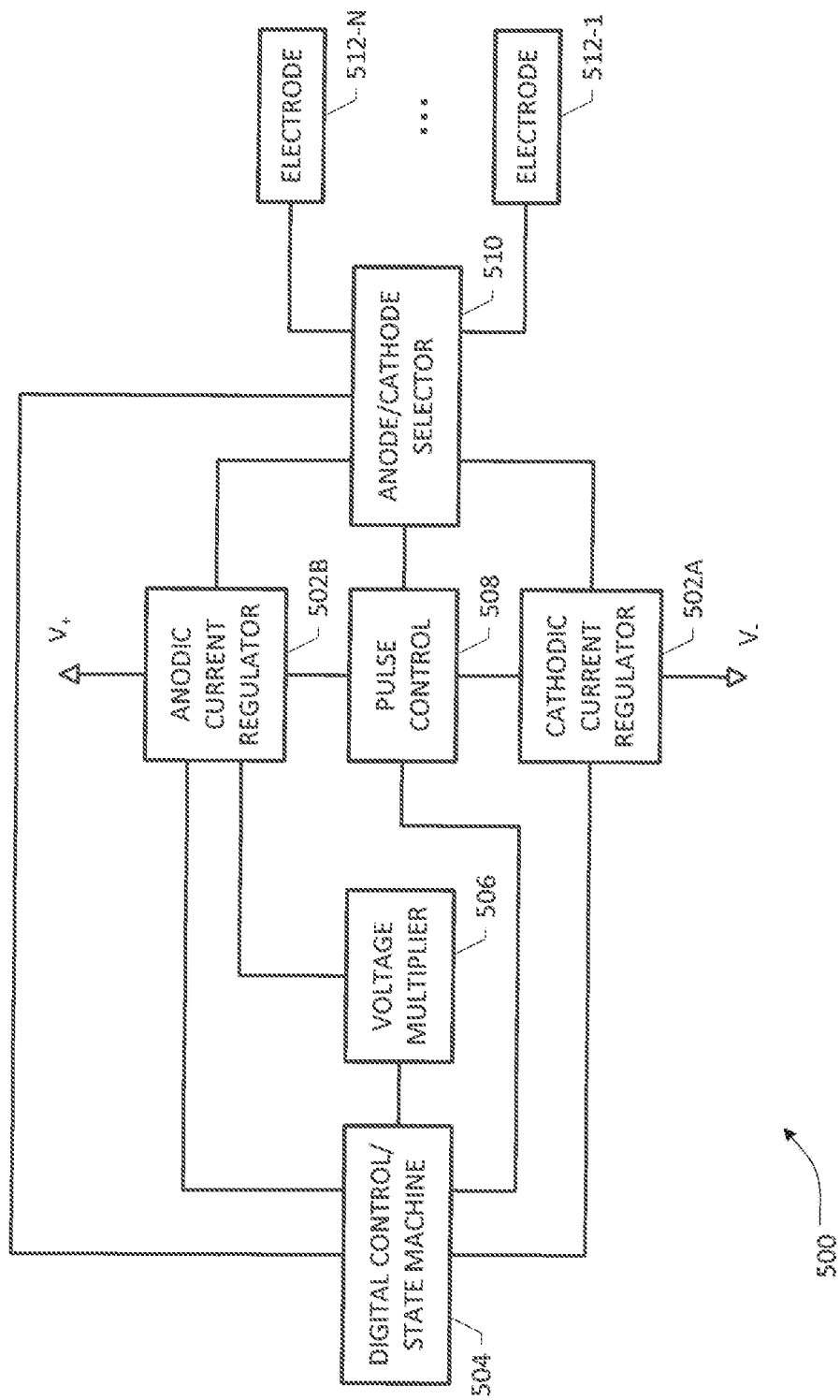
FIG. 5 depict a block diagram of an example pulse generator system wherein a current regulator of the present disclosure may be configured to provide cathodic and/or anodic stimulation current to a biological tissue.

FIG. 5 depicts a block diagram of an example pulse generator system 500 wherein embodiments of the present disclosure may be configured to provide split stimulation current to a biological tissue in either cathodic or anodic stimulation. A digital control logic block 504 (which may be implemented as a state machine in some implementations) may be programmed to provide suitable digital control signals to a cathodic current regulator 502A and an anodic current regulator 502B, which may be configured to provide respective split current segments as described above. A voltage multiplier 506 may be configured to operate responsive to control signals from the digital control logic block 504 with respect to the generation of appropriate stimulation pulses under pulse control 508. A polarity selector 510 is coupled to the cathodic and anodic current regulators 502A/502B for selectively providing, under programmatic control signaling from digital control module 504, either cathodic split current segments or anodic split current segments to at least a subset of lead electrodes 512-1 to 512-N.

Skilled artisans will appreciate that cathodic and anodic current regulators 502A/502B may be configured to operate with respective current sources/sinks as well as current return paths in an IPG implementation, as is known in the art. For instance, depending on anodic or cathodic stimulation, the electrodes may be selectively tied to respective DAC circuitry configured to operate as current sources or current sinks in a current regulator arrangement in accordance with the teachings herein. As noted previously, an anodic current regulator arrangement may be formed of PMOS devices given that the source may be biased to a high voltage (V+), whereas a cathodic current regulator arrangement may be formed of NMOS devices where the sink is biased to a low voltage (V−), with respective substrate connections typically tied to a suitable power supply or to respective transistor source nodes. Other modifications as to, e.g., gate driver logic levels, device sizing (based on $I_{DS}$ handling requirements), among others, may be applied, mutatis mutandis, in a typical implementation depending on whether anodic or cathodic current stimulation architecture is involved.

Figure 6A:
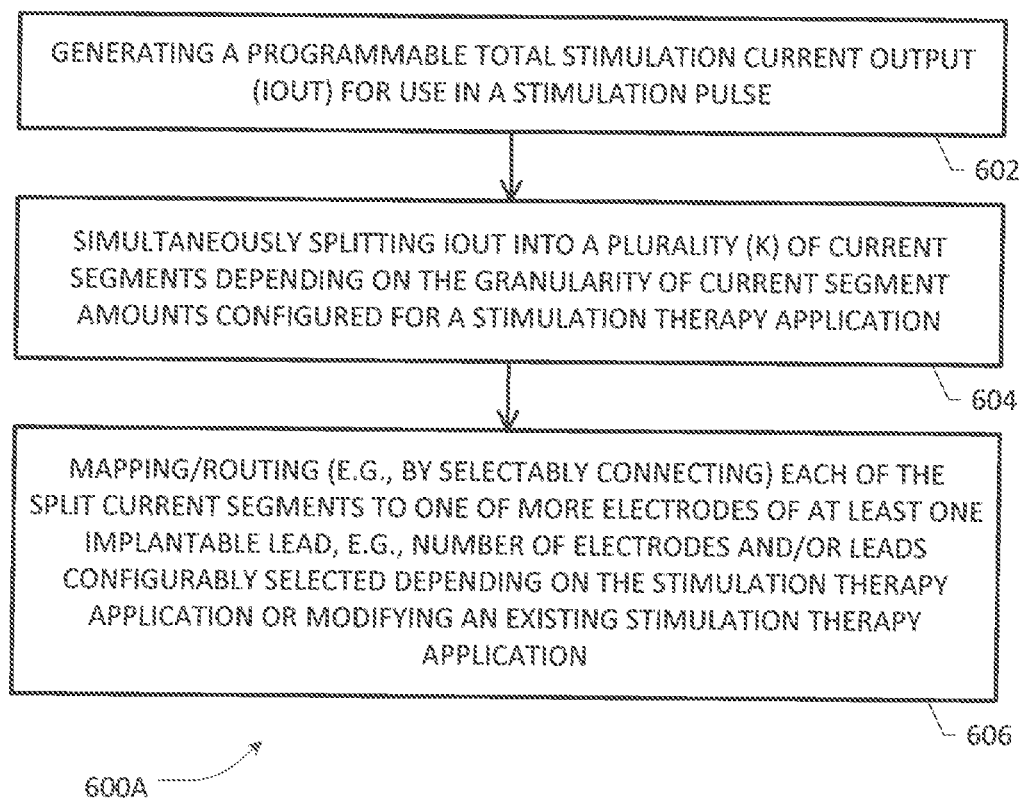
FIGS. 6A-6C depict flowcharts illustrative of blocks, steps and/or acts that may be (re)combined in one or more arrangements for effectuating simultaneous splitting of stimulation current according to an embodiment of the present disclosure.
Figure 6B:
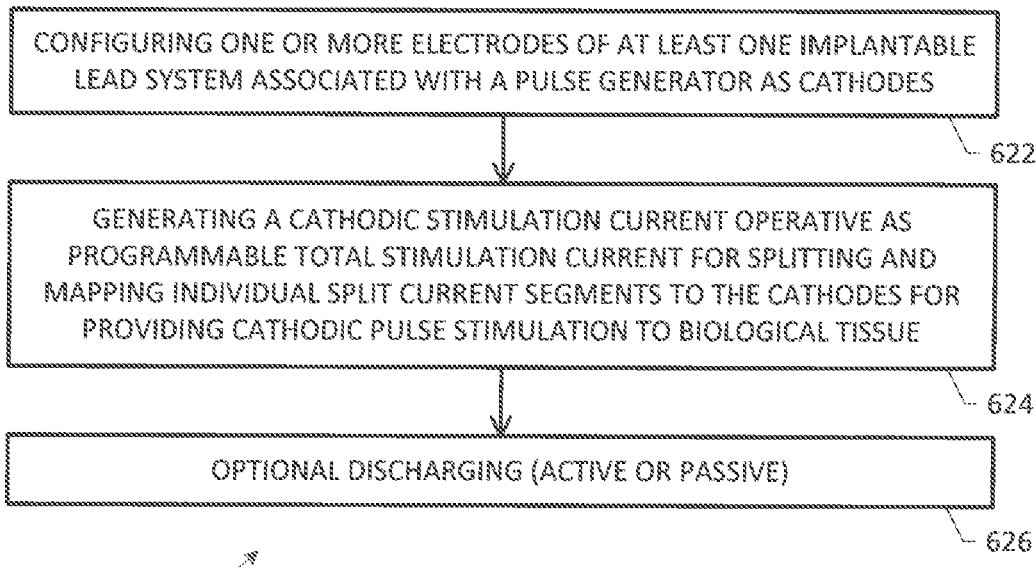
Figure 6C:
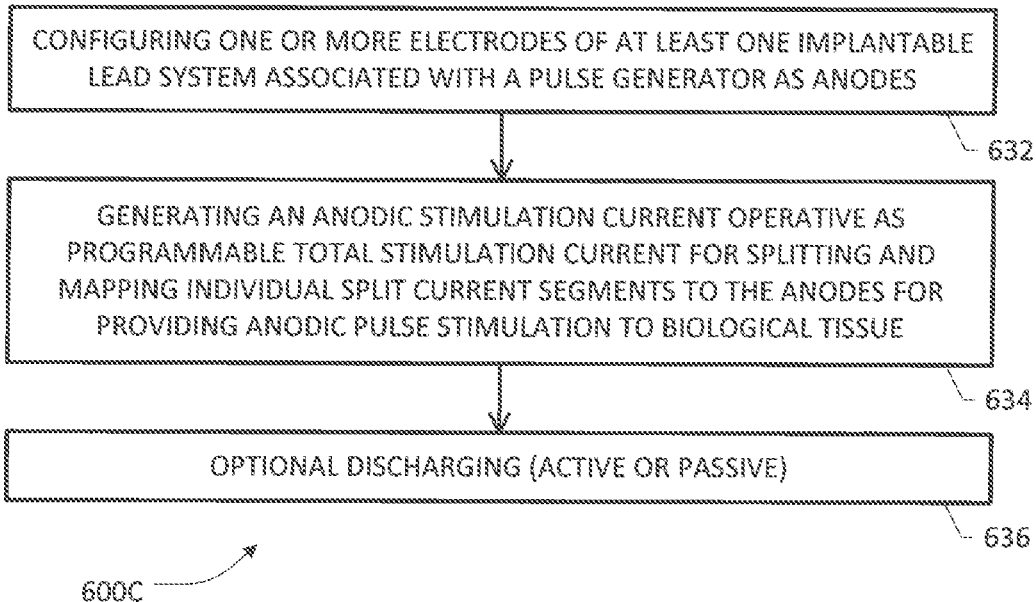

FIGS. 6A-6C depict flowcharts illustrative of blocks, steps and/or acts that may be (re)combined in one or more arrangements, with or without blocks, steps and/or acts of additional flowcharts of the present disclosure, for effectuating simultaneous splitting of stimulation current according to an embodiment. As illustrated in FIG. 6A, process 600A may commence with generating a programmable total stimulation current output (IOUT) for use in a stimulation pulse (block 602). At block 604, the total stimulation current output (IOUT) is simultaneously split into a plurality (K) of current segments depending on the granularity of current segment amounts configured for a stimulation therapy application. As noted previously, the split current segments need not comprise equal fractions of the stimulation current. At block 606, each of the split current segments may be selectively mapped to one or more electrodes of at least one implantable lead, wherein a select number of electrodes and/or leads may be configurably selected depending on the stimulation therapy application or modifying an existing stimulation therapy application. Process 600B shown in FIG. 6B relates to a process flow with respect to cathodic stimulation of a biological tissue. At block 622, one or more electrodes of an implantable lead system (having one or more leads) associated with a pulse generator may be configured as cathodes, wherein a suitable anodic terminal may be provided to effectuate the current loop path. At block 624, a cathodic stimulation current operative as a programmable total stimulation current may be generated, which may be for split into a number of cathodic split current segments that may be mapped to the cathodes for providing cathodic pulse stimulation to the biological tissue. At block 626, an optional discharging process (either active or passive) may be effectuated, e.g., depending on charge accumulation, as noted previously. Process 600C shown in FIG. 6C relates to a process flow with respect to anodic stimulation of a biological tissue. At block 632, one or more electrodes of an implantable lead system (having one or more leads) associated with a pulse generator may be configured as anodes, with a suitable cathodic terminal implemented to effectuate the current loop. At block 634, an anodic stimulation current operative as a programmable total stimulation current may be generated, which may be for split into a number of anodic split current segments that may be mapped to the anodes for providing anodic pulse stimulation to the biological tissue. Similar to the cathodic stimulation process 600B above, an optional discharging process (either active or passive) may be effectuated for discharging any charge accumulated over one or more anodic stimulation cycles (block 636).

Figure 7:
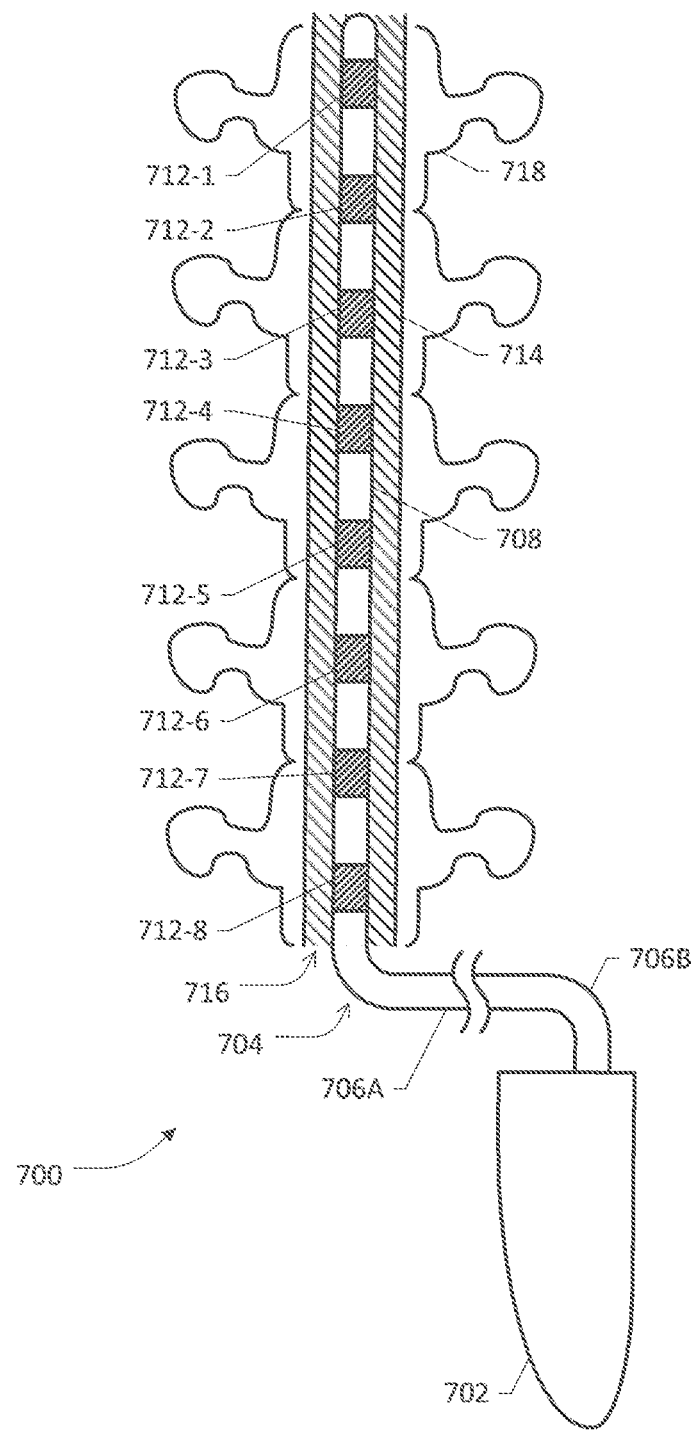
FIG. 7 illustrates an example spinal cord stimulation (SCS) therapy application involving a pulse generator and associated lead system having a plurality of electrodes that may be stimulated using an embodiment of a current regulator of the present disclosure.

FIG. 7 illustrates an example spinal cord stimulation (SCS) therapy application system 700 involving a pulse generator 702 and associated lead system 704 having a plurality of electrodes 712-1 to 712-8 that may be selectively stimulated using an embodiment of a current regulator of the present disclosure. Preferably, the lead system 704 comprises a lead body 706A/B coupled to an implantable lead 708 that may be positioned at a desired target position in an epidural space 716 defined by a plurality of vertebrae of a patient so as to be in close proximity to a nerve tissue of interest, e.g., a spinal cord 714. The implantable lead 708 includes eight electrodes 712-1 to 712-8, which may comprise ring electrodes, segmented electrodes, and the like that may be separated from one another by equal or unequal portions of encapsulating material. The implantable lead 708 is connected via lead body 706A/706B to the pulse generator or IPG 702 that includes at least an embodiment of a current regulator of the present disclosure configured to provide a plurality of split current segments for cathodic or anodic stimulation. As noted previously, at least a subset of the electrodes 712-1 to 712-8 may be selectively energized, i.e., stimulated, wherein a total stimulation current output may be split into uniform or non-uniform fractions. For example, electrodes 712-1, 712-4 and 712-8 may be programmed as cathodes or anodes for operation in conjunction with the case or can of the IPG 702 for providing split current stimulation to effectuate an electric field that is spatially distributed over entire target portion of the spinal cord 714.

It should be appreciated that although the lead system 704 is exemplified in the above implementation with a single implantable lead, IPG 702 may be configured with a current regulator to split a stimulation current into a number of split current segments (having equal or unequal amounts of split current segments) that may be mapped to a plurality of electrodes across multiple leads in different combinations depending on the desired stimulation therapy.

Based on the foregoing Detailed Description, skilled artisans will recognize that embodiments of the present patent disclosure facilitate a current regulation scheme for splitting pulsed stimulation current in a biostimulation system (e.g., provided by a single constant current source) in a dynamically configurable manner so as to provide a fine-tuned adjustment to the electric field generated proximate to or over a target tissue via one or more implantable leads. Accordingly, optimal shaping of the electric field around the target tissue (e.g., neural tissue) requiring therapeutic stimulation may be effectuated, whereby therapeutic benefits to the patient may be enhanced. In addition, because of the high degree of granularity provided in current splitting via suitable programmatic control, the incidence of undesirable collateral effects in a stimulation therapy may be minimized. Further, optimization of therapy based on implementing an embodiment of the present patent disclosure may not only help better personalize and individualize a treatment targeted to a particular patient and the patient's physiognomy but also help to enhance the electrical efficiency of delivering stimulation pulses, thereby improving the battery longevity of an implanted biostimulation system. Still further, should an implantable lead undergo misalignment, misplacement, and/or migration (e.g., due to the patient's physical activity or otherwise), the need for having to resort to surgical procedures may be advantageously obviated because of the ability of an embodiment to readjust and/or reshape the electric field distribution in order to maintain optimum stimulation therapy for the patient.

In the above-description of various embodiments of the present disclosure, it is to be understood that the terminology used herein is for the purpose of describing particular embodiments only and is not intended to be limiting of the invention. Unless otherwise defined, all terms (including technical and scientific terms) used herein have the same meaning as commonly understood by one of ordinary skill in the ad to which this invention belongs. It will be further understood that terms, such as those defined in commonly used dictionaries, should be interpreted as having a meaning that is consistent with their meaning in the context of this specification and the relevant art and may not be interpreted in an idealized or overly formal sense expressly so defined herein.

At least some example embodiments are described herein with reference to one or more circuit diagrams/schematics, block diagrams and/or flowchart illustrations. It is understood that such diagrams and/or flowchart illustrations, and combinations of blocks in the block diagrams and/or flowchart illustrations, can be implemented by any appropriate circuitry configured to achieve the desired functionalities. Accordingly, example embodiments of the present disclosure may be embodied in hardware and/or in software (including firmware, resident software, micro-code, etc.) operating in conjunction with suitable processing units or microcontrollers, which may collectively be referred to as "circuitry," "a module" or variants thereof. An example processing unit or a module may include by way of illustration, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Array (FPGA) circuits, any other type of integrated circuit (IC), and/or a state machine, as well as programmable system devices (PSDs)

employing system-on-chip (SoC) architectures that combine memory functions with programmable logic on a chip that is designed to work with a standard microcontroller. Example memory modules or storage circuitry may include volatile and/or nonvolatile memories such as, e.g., random access memory (RAM), electrically erasable/programmable read-only memories (EEPROMs) or UV-EPROMS, one-time programmable (OTP) memories, Flash memories, static RAM (SRAM), etc.

Further, in at least some additional or alternative implementations, the functions/acts described in the blocks may occur out of the order shown in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Furthermore, although some of the diagrams include arrows on communication paths to show a primary direction of communication, it is to be understood that communication may occur in the opposite direction relative to the depicted arrows. Finally, other blocks may be added/inserted between the blocks that are illustrated.

It should therefore be clearly understood that the order or sequence of the acts, steps, functions, components or blocks illustrated in any of the flowcharts depicted in the drawing Figures of the present disclosure may be modified, altered, replaced, customized or otherwise rearranged within a particular flowchart, including deletion or omission of a particular act, step, function, component or block. Moreover, the acts, steps, functions, components or blocks illustrated in a particular flowchart may be inter-mixed or otherwise inter-arranged or rearranged with the acts, steps, functions, components or blocks illustrated in another flowchart in order to effectuate additional variations, modifications and configurations with respect to one or more processes for purposes of practicing the teachings of the present patent disclosure.

Although various embodiments have been shown and described in detail, the claims are not limited to any particular embodiment or example. None of the above Detailed Description should be read as implying that any particular component, element, step, act, or function is essential such that it must be included in the scope of the claims. Reference to an element in the singular is not intended to mean "one and only one" unless explicitly so stated, but rather "one or more." All structural and functional equivalents to the elements of the above-described embodiments that are known to those of ordinary skill in the art are expressly incorporated herein by reference and are intended to be encompassed by the present claims. Accordingly, those skilled in the art will recognize that the exemplary embodiments described herein can be practiced with various modifications and alterations within the spirit and scope of the claims appended below.

The invention claimed is:

1. A pulse generator for stimulating biological tissue, comprising:
a power supply module; and
a processing unit operative with a digital control logic module to provide control signals to a current regulator comprising:
a digitally-programmable analog voltage generator operative with the power supply module to provide a voltage output signal to a first input of an error amplifier configured to generate a programmable total stimulation current output;
a programmable resistor network configured to control an input signal provided to a second input of the error amplifier responsive to the programmable total stimulation current output;
a plurality of current splitting switches operative to simultaneously split the programmable total stimulation current output into a corresponding plurality of split current segments; and
current mapping circuitry, operative in response to one or more digital control signals generated by at least one electrode select logic module forming a decode block, the current mapping circuitry configured to selectively connect each simultaneously split current segment to any of one or more electrodes of an implantable lead system having at least one implantable lead, each lead having a plurality of electrodes, wherein an electrode is operative, when activated, to apply a portion of the programmable total stimulation current output for stimulating the biological tissue depending on an electrical connection relationship determined by the current mapping circuitry.

2. The pulse generator as recited in claim 1, wherein the portion of the programmable total stimulation current output applied at an electrode comprises a sum of all individual split current segments to which the electrode is connected during a stimulation pulse responsive to the one or more digital control signals asserted by the decode block to control the current mapping circuitry.

3. The pulse generator as recited in claim 2, wherein the current regulator comprises a cathodic current regulator configured to provide a cathodic stimulation current operative as the programmable total stimulation current output simultaneously split into a plurality of cathodic current segments, each of which is mapped to the one or more electrodes configured to operate as one or more cathode terminals of the implantable lead system.

4. The pulse generator as recited in claim 2, wherein the current regulator comprises an anodic current regulator configured to provide an anodic stimulation current operative as the programmable total stimulation current output simultaneously split into a plurality of anodic current segments, each of which is mapped to the one or more electrodes configured to operate as one or more anode terminals of the implantable lead system.

5. The pulse generator as recited in claim 2, wherein the current mapping circuitry comprises a plurality of banks of mapping elements, each bank associated with a corresponding one of the split current segments, and further wherein each bank comprises a set of mapping elements equal to the number of the plurality of electrodes.

6. The pulse generator as recited in claim 5, wherein the plurality of current splitting switches comprise identically sized transistor elements for splitting the programmable total stimulation current output into equal fractions of current with respect to the plurality of split current segments.

7. The pulse generator as recited in claim 5, wherein the plurality of current splitting switches comprise differently sized transistor elements for splitting the programmable total stimulation current output into unequal fractions of current with respect to the plurality of split current segments.

8. The pulse generator as recited in claim 5, wherein each bank of mapping elements is controlled by a corresponding electrode select logic module of the decode block, the corresponding electrode select logic module operating responsive to a respective digital control signal of $\log_2\{N\}$ bits, where N is the number of the plurality of electrodes.

9. The pulse generator as recited in claim 8, wherein each electrode select logic module is configured to decode the respective digital control signal of $\log_2\{N\}$ bits to assert a single control signal to enable mapping of a split current segment to a single electrode.

10. The pulse generator as recited in claim 8, wherein each electrode select logic module is configured to decode the respective digital control signal of $\log_2\{N\}$ bits to assert a set of control signals to enable mapping of a split current segment to a corresponding set of the plurality of the electrodes.

11. A method operative with a pulse generator for stimulating biological tissue, the method comprising:
generating a programmable total stimulation current output for a stimulation pulse;
simultaneously splitting the programmable total stimulation current output into a plurality of split current segments; and
selectively mapping each of the simultaneously split current segments to connect to any of one or more electrodes of an implantable lead system having at least one implantable lead, each lead having a plurality of electrodes, wherein an electrode is operative, when activated, to apply a portion of the programmable total stimulation current output for stimulating the biological tissue depending on an electrical connection relationship determined by current mapping circuitry operative in response to one or more digital control signals generated by a decode block,
wherein the programmable total stimulation current output is split into a plurality of configurable fractions corresponding to the plurality of split current segments depending on a stimulation setting configured for a particular stimulation therapy application with respect to the biological tissue,
wherein the portion of the programmable total stimulation current output applied at an electrode comprises a sum of all individual split current segments to which the electrode is connected during the stimulation pulse responsive to the one or more digital control signals asserted by the decode block to control the current mapping circuitry,
wherein a plurality of banks of mapping elements are provided for forming the current mapping circuitry, each bank associated with a corresponding one of the split current segments, and further wherein each bank comprises a set of mapping elements equal to the number of the plurality of electrodes, and
wherein a plurality of electrode select logic modules are provided corresponding to the plurality of banks of mapping elements, the plurality of electrode select logic modules forming the decode block, each electrode select logic module operating responsive to a respective digital control signal of $\log_2\{N\}$ bits, where N is the number of the plurality of electrodes.

12. The method as recited in claim 11, further comprising:
configuring the one or more electrodes as one or more cathode terminals of the implantable lead system; and
generating a cathodic stimulation current operative as the programmable total stimulation current output simultaneously split into a plurality of cathodic current segments, each of which is mapped to the one or more electrodes configured to operate as the one or more cathode terminals.

13. The method as recited in claim 11, further comprising:
configuring the one or more electrodes as one or more anode terminals of the implantable lead system; and
generating an anodic stimulation current operative as the programmable total stimulation current output simultaneously split into a plurality of anodic current segments, each of which is mapped to the one or more electrodes configured to operate as the one or more anode terminals.

14. The method as recited in claim 11, wherein the plurality of split current segments comprise equal current fractions.

15. The method as recited in claim 11, wherein the plurality of split current segments comprise unequal current fractions.

16. The method as recited in claim 11, further comprising:
decoding the respective digital control signal of $\log_2\{N\}$ bits by each corresponding electrode select logic module to assert a single control signal to enable mapping of a split current segment to a single electrode.

17. The method as recited in claim 11, further comprising:
decoding the respective digital control signal of $\log_2\{N\}$ bits by each corresponding electrode select logic module to assert a set of control signals to enable mapping of a split current segment to a corresponding set of the plurality of electrodes.

18. A biostimulation system operative to provide stimulation therapy to a patient, the system comprising:
a pulse generator; and
an implantable lead system coupled to the pulse generator, the lead system including at least one implantable lead having a plurality of electrodes,
wherein the pulse generator includes:
a power supply module; and
a processing unit operative with a digital control logic module to provide control signals to a current regulator comprising:
a digitally-programmable analog voltage generator operative with the power supply module to provide a voltage output signal to a first input of an error amplifier configured to generate a programmable total stimulation current output;
a programmable resistor network configured to control an input signal provided to a second input of the error amplifier responsive to the programmable total stimulation current output;
a plurality of current splitting switches operative to simultaneously split the programmable total stimulation current output into a corresponding plurality of split current segments; and
current mapping circuitry, operative in response to one or more digital control signals generated by at least one electrode select logic module forming a decode block, the current mapping circuitry configured to selectively connect each simultaneously split current segment to any of one or more electrodes of the implantable lead system, wherein an electrode is operative, when activated, to apply a portion of the programmable total stimulation current output for stimulating a tissue of the patient depending on an electrical connection relationship determined by the current mapping circuitry.

19. The system as recited in claim 18, wherein the portion of the programmable total stimulation current output applied at an electrode comprises a sum of all individual split current segments to which the electrode is connected during a stimulation pulse responsive to the one or more digital control signals asserted by the decode block to control the current mapping circuitry.

20. The system as recited in claim 19, wherein the current mapping circuitry comprises a plurality of banks of mapping elements, each bank associated with a corresponding one of the split current segments, and further wherein each bank comprises a set of mapping elements equal to the number of the plurality of electrodes.

21. The system as recited in claim 20, wherein the plurality of current splitting switches comprise identically sized transistor elements for splitting the programmable total stimulation current output into equal fractions of current with respect to the plurality of split current segments.

22. The system as recited in claim 20, wherein the plurality of current splitting switches comprise differently sized transistor elements for splitting the programmable total stimulation current output into unequal fractions of current with respect to the plurality of split current segments.

23. The system as recited in claim 20, wherein each bank of mapping elements is controlled by a corresponding electrode select logic module of the decode block, the corresponding electrode select logic module operating responsive to a respective digital control signal of $\log_2\{N\}$ bits, where N is the number of the plurality of electrodes.

24. The system as recited in claim 23, wherein each electrode select logic module is configured to decode the respective digital control signal of $\log_2\{N\}$ bits to assert a single control signal to enable mapping of a split current segment to a single electrode.

25. The system as recited in claim 23, wherein each electrode select logic module is configured to decode the respective digital control signal of $\log_2\{N\}$ bits to assert a set of control signals to enable mapping of a split current segment to a corresponding set of the plurality of the electrodes.

* * * * *